(12) United States Patent
Rausch et al.

(10) Patent No.: US 10,755,556 B2
(45) Date of Patent: Aug. 25, 2020

(54) INTERRUPT DETECTION FOR PHYSIOLOGICAL SENSOR

(71) Applicant: Nonin Medical, Inc., Plymouth, MN (US)

(72) Inventors: Gregory J. Rausch, Minnetonka, MN (US); Hugh Ferguson, Blaine, MN (US); David Lee Lemke, Victoria, MN (US)

(73) Assignee: Nonin Medical, Inc., Plymouth, MN (US)

( * ) Notice: Subject to any disclaimer, the term of this patent is extended or adjusted under 35 U.S.C. 154(b) by 0 days.

(21) Appl. No.: 15/515,536

(22) PCT Filed: Sep. 29, 2015

(86) PCT No.: PCT/US2015/052801
§ 371 (c)(1),
(2) Date: Mar. 29, 2017

(87) PCT Pub. No.: WO2016/053943
PCT Pub. Date: Apr. 7, 2016

(65) Prior Publication Data
US 2017/0221349 A1    Aug. 3, 2017

Related U.S. Application Data

(60) Provisional application No. 62/057,068, filed on Sep. 29, 2014.

(51) Int. Cl.
*G08B 21/00*       (2006.01)
*G08B 29/18*       (2006.01)
(Continued)

(52) U.S. Cl.
CPC .......... *G08B 29/185* (2013.01); *A61B 5/0022* (2013.01); *A61B 5/01* (2013.01);
(Continued)

(58) Field of Classification Search
CPC .. G08B 21/0286; G08B 21/00; G08B 29/046; A61B 5/00; A61B 5/18; A61B 5/6843;
(Continued)

(56) References Cited

U.S. PATENT DOCUMENTS 6,453,184 B1 * 9/2002 Hyogo ............... A61B 5/14551
600/323
6,801,799 B2 * 10/2004 Mendelson ........ A61B 5/14552
600/322

(Continued)

FOREIGN PATENT DOCUMENTS

JP    H07194581 A    8/1995
JP    200107899 A    3/2001
(Continued)

OTHER PUBLICATIONS

International Application Serial No. PCT/US2015/052801, International Search Report dated Dec. 29, 2015, 2 pgs.
(Continued)

*Primary Examiner* — Julie B Lieu
(74) *Attorney, Agent, or Firm* — Schwegman Lundberg & Woessner, P.A.

(57) ABSTRACT

A device includes a housing, an emitter, a detector, and a processor. The housing has a body contact surface configured for affixation to a tissue site of a body. The emitter is coupled to the housing and has an emission surface and an electrical terminal. The emission surface is configured to emit light proximate the body contact surface in response to a signal applied to the electrical terminal. The detector is coupled to the housing. The detector has a sense surface and an output terminal. The detector is configured to provide an output signal on the output terminal in response to light detected at the sensor surface. The processor is coupled to the electrical terminal and coupled to the output terminal. The processor is configured to implement an algorithm to (Continued)

monitor for an interruption between the body contact surface and the body and configured to generate an interrupt signal corresponding to the monitoring.

13 Claims, 4 Drawing Sheets

(51) Int. Cl.
  *A61B 5/01* (2006.01)
  *A61B 5/053* (2006.01)
  *A61B 5/1455* (2006.01)
  *A61B 5/00* (2006.01)

(52) U.S. Cl.
  CPC .......... *A61B 5/053* (2013.01); *A61B 5/14551* (2013.01); *A61B 5/6831* (2013.01); *A61B 5/6843* (2013.01); *A61B 5/742* (2013.01); *A61B 5/7405* (2013.01); *A61B 5/7455* (2013.01); *A61B 5/4833* (2013.01); *A61B 2560/0462* (2013.01); *A61B 2562/0214* (2013.01); *A61B 2562/0247* (2013.01); *A61B 2562/0271* (2013.01)

(58) Field of Classification Search
  CPC ......... A61B 5/6844; A61B 5/053; A61B 5/72; A61B 5/7221; A61B 5/7282; A61B 5/74; A61B 5/746; A61B 5/4806; A61B 5/4809; A61B 5/4815
  See application file for complete search history.

(56) References Cited

U.S. PATENT DOCUMENTS

| | | | | |
|---|---|---|---|---|
| 6,890,304 | B1* | 5/2005 | Amano | A61B 5/02 600/500 |
| 7,894,869 | B2* | 2/2011 | Hoarau | A61B 5/14552 600/323 |
| 8,401,602 | B2* | 3/2013 | Kiani | A61B 5/061 600/310 |
| 8,410,926 | B1* | 4/2013 | Gary, Jr. | A61B 5/002 340/539.12 |
| 2003/0071734 | A1* | 4/2003 | Vodin | F41H 9/00 340/573.1 |
| 2014/0275813 | A1* | 9/2014 | Stivoric | A61B 5/0205 600/300 |
| 2014/0275852 | A1* | 9/2014 | Hong | A61B 5/02427 600/301 |
| 2015/0094552 | A1* | 4/2015 | Golda | A61B 5/04325 600/336 |
| 2015/0223705 | A1* | 8/2015 | Sadhu | G01S 19/17 600/301 |

FOREIGN PATENT DOCUMENTS

| | | |
|---|---|---|
| JP | 2009022639 A | 2/2009 |
| JP | 2010088487 A | 4/2010 |
| JP | 2010220948 A | 10/2010 |
| WO | WO-0056209 A1 | 9/2000 |
| WO | WO-0228274 A1 | 4/2002 |
| WO | WO-2012021900 A1 | 2/2012 |
| WO | WO-2016053943 A1 | 4/2016 |

OTHER PUBLICATIONS

International Application Serial No. PCT/US2015/052801, Written Opinion dated Dec. 29, 2015, 5 pgs.
International Application Serial No. PCT/US/2015/052801, International Preliminary Report on Patentability dated Apr. 13, 2017, 7 pgs.
Japanese Application Serial No, 2017-516704, Office Action dated Aug. 6, 2019, w/ English Translation. 7 pgs.
"Japanese Application Serial No. 2017-516704, Response filed Feb. 5, 2020 to Office Action dated Aug. 6, 2019", w/ English Claims, 9 pgs.

* cited by examiner

INTERRUPT DETECTION FOR PHYSIOLOGICAL SENSOR

CLAIM OF PRIORITY

This patent application is a U.S. National Stage Filing under 35 U.S.C. 371 from International Application No. PCT/US2015/052801, filed on Sep. 29, 2015, and published as WO 2016/053943 A1 on Apr. 7, 2016, which claims the benefit of priority of U.S. Provisional Patent Application Ser. No. 62/057,068, filed on Sep. 29, 2014, each of which is hereby incorporated by reference herein in its entirety.

BACKGROUND

For certain workers, medical and health complications can lead to public safety risks. For example, some transportation workers (such as truck drivers) are subject to regulation and are required to meet certain sleep requirements to ensure alert performance.

A home sleep test (HST) is sometimes used to determine compliance with rest requirements. The HST typically includes wearing a device for a specified period of time. The results of a HST, however, can be compromised by tampering with the sensor device or by improperly substituting a different test subject.

One effort to mitigate tampering or substitution includes equipping a device with a mechanical lock. Such efforts have been inadequate.

Overview

The present inventors have recognized, among other things, that a problem to be solved can include providing a convenient means of preventing tampering or substitution. The present subject matter can help provide a solution to this problem, such as by providing a physiological sensor that can detect tampering or substitution.

A device includes a housing, an emitter, a detector, and a processor. The housing has a body contact surface configured for affixation to a tissue site of a body. The emitter is coupled to the housing and has an emission surface and an electrical terminal. The emission surface is configured to emit light proximate the body contact surface in response to a signal applied to the electrical terminal. The detector is coupled to the housing. The detector has a sense surface and an output terminal. The detector is configured to provide an output signal on the output terminal in response to light detected at the sensor surface. The processor is coupled to the electrical terminal and coupled to the output terminal. The processor is configured to implement an algorithm to monitor for an interruption between the body contact surface and the body and configured to generate an interrupt signal corresponding to the monitoring.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
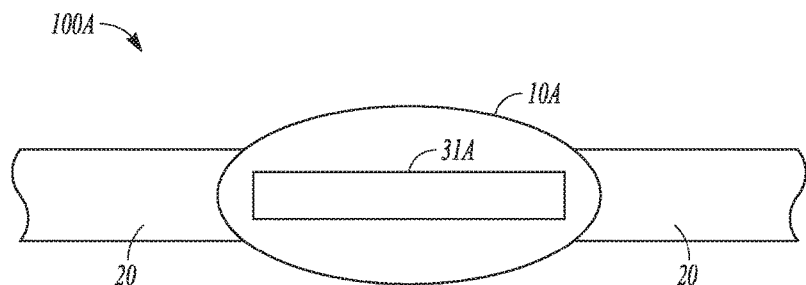
FIG. 1 includes a view of a wearable system, according to one example.
Figure 2:
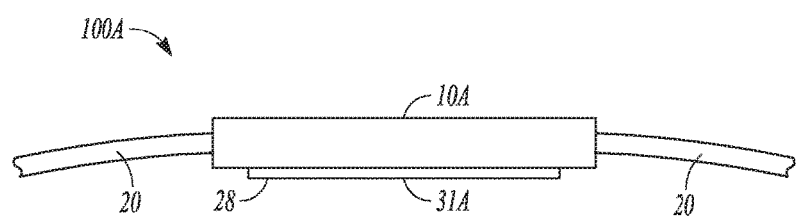
FIG. 2 includes a view of a wearable system, according to one example.

FIG. 1 and FIG. 2 include views of wearable system 100A, according to one example. System 100A includes device 10A coupled to belt 20. Device 10A includes sensor 31A disposed on contact surface 28. Belt 20 includes a flexible strap material and is configured to encircle a portion (such as an arm, a leg, a chest) of a user and maintain a close physical coupling between the user and contact surface 28. Belt 20 can include an adjuster, a clip, a fastener, a buckle, or other structure to secure device 10A in a specified location on a user. Device 10A has an oval form factor in the example illustrated, however, other shapes and configurations are also contemplated.

Sensor 31A is configured to generate an output signal corresponding to a physiological parameter. Sensor 31A can include an optical element, a proximity detector, an electrode, or other element.

Figure 3A:
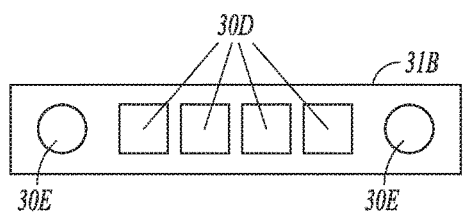
FIG. 3A includes a view of sensor, according to one example.

FIG. 3A includes a view of sensor 31B having optical elements, according to one example. Sensor 31B includes two optical emitters, each of which are denoted as emitter 30E, and four detectors, each of which are denoted as detectors 30D. The optical elements of sensor 31B are arranged in a linear alignment but other configurations or number of elements are also contemplated.

Figure 3B:
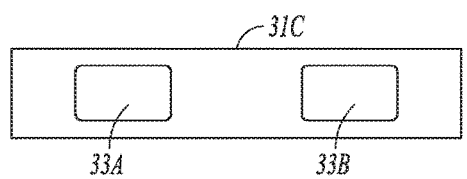
FIG. 3B includes a view of sensor, according to one example.

FIG. 3B includes a view of sensor 31C, according to one example. Sensor 31C includes sensor surfaces 33A and 33B. Sensor surfaces 33A and 33B can include electrodes, touch-sensors, optical elements, or other components configured to provide a signal by which the present subject matter can determine a physiological parameter.

Figure 4A:
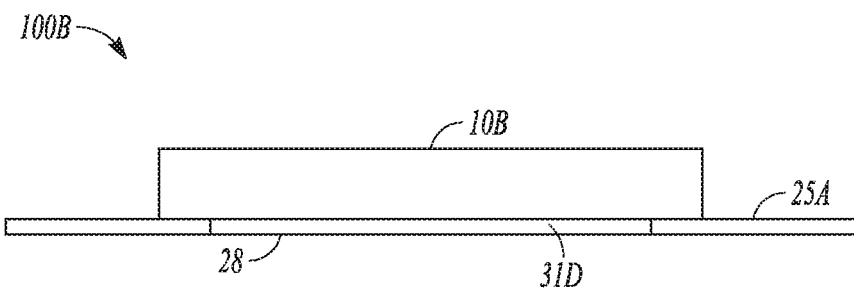
FIG. 4A includes a view of system, according to one example.

FIG. 4A includes a view of system 100B, according to one example. System 100B includes device 10B affixed to membrane 25A. Contact surface 28 of membrane 25A is configured to couple with a tissue site using an adhesive bond. Device 10B includes sensor 31D. Sensor 31D is configured to generate a signal corresponding to a physiological parameter.

Figure 4B:
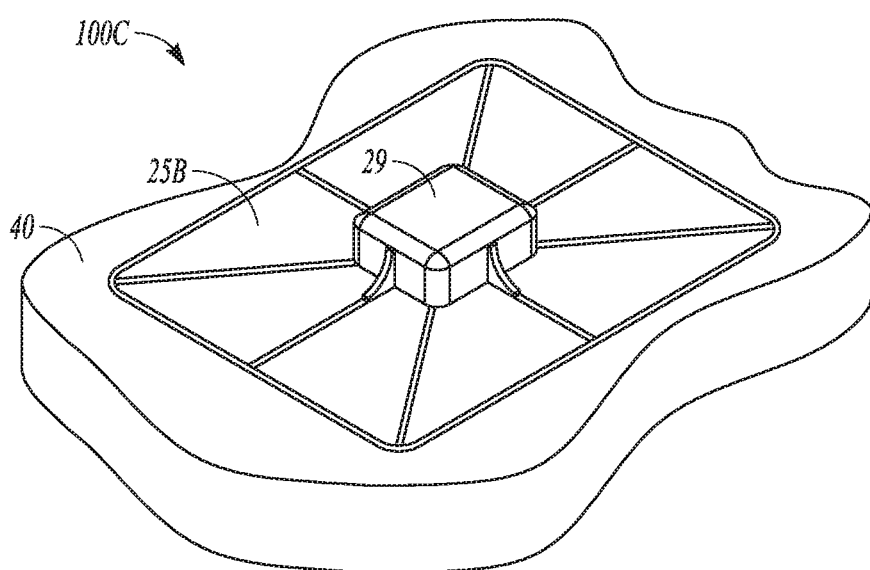
FIG. 4B includes a view of system, according to one example.

FIG. 4B includes a view of system 100C, according to one example. System 100C includes receiver 29 configured accept a sensor, such as sensor 31A, 31B, or 31C. Receiver 29, sometimes referred to as a sensor pocket, is affixed to membrane 25B. In the example shown, receiver 29 is reinforced by support ribs abutting membrane 25B. The figure illustrates system 100C coupled to tissue 40. Membrane 25B abuts tissue 40 at a contact surface and in one example, the contact surface is bonded with an adhesive. Membrane 25B can include a foam material, an elastomer or textile pad. Receiver 29 obstructs a view of a sensor in this figure. Membrane 25B can be affixed to the tissue site by an adhesive layer.

Figure 5:
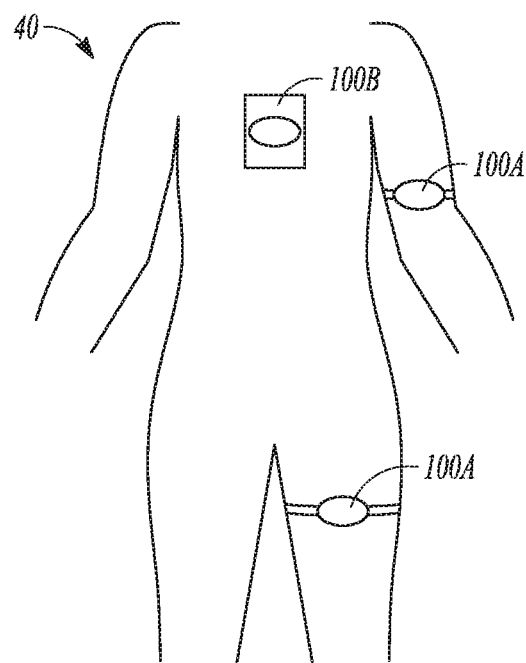
FIG. 5 includes a view of a user fitted with a system, according to one example.

FIG. 5 includes a view of user 40 fitted with a plurality of systems, according to one example. System 100B is affixed at a tissue site at the chest of user 40 and is coupled by an adhesive bond. User 40 is shown fitted with first system 100A affixed at a tissue site on a bicep and a second system 100A affixed at a tissue site on a thigh. The first system 100A and the second system 100A are affixed by a belt in the figure. This figure illustrates various examples and in a particular application, only a single system would be affixed to a user, however, more than one system may be used in a particular circumstance.

Figure 6:
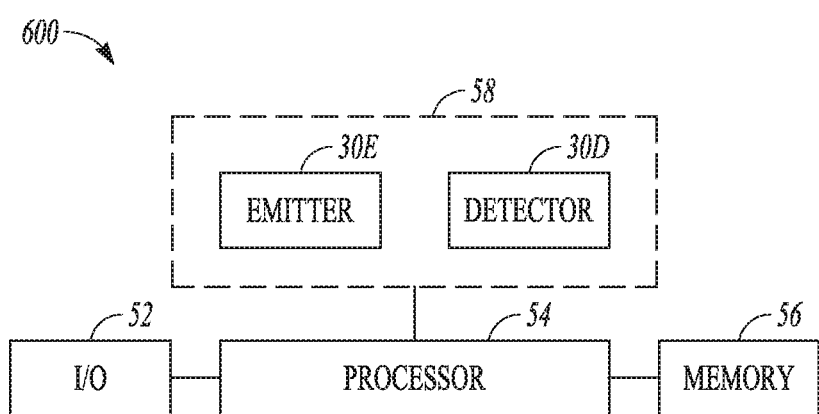
FIG. 6 includes a block diagram of a system, according to one example.

FIG. 6 includes a block diagram of system 600, according to one example. System 600 represents an example of a sensor, such as sensor 31B. System 600 is configured for affixation to tissue at a site. System 600 is non-invasive and includes input/output module 52, processor 54, memory 56, and optical module 58. Optical module 58 includes optical emitter 30E and optical detector 30D.

Input/output module 52 can include a power switch, a mode control switch, a display, a user-control, a touchscreen, an indicator light, or other interface elements that enable a user to interact with system 600. Input/output module 52 can include a wireless interface to allow communication with a remote device.

Processor 54 can include an analog processor. In one example, processor 54 includes a digital processor and is configured to execute instructions for implementing an algorithm. The instructions and data can be stored in memory 56. Processor 54 can include an analog front end having an amplifier, a filter, a sample and hold circuit, an analog-to-digital converter (ADC), a digital-to-analog converter (DAC), an LED driver, or other modules.

Emitter 30E can include a light emitting diode (LED) configured to emit light of a selected wavelength and power. Detector 30D can include a photodiode.

Light energy emitted by optical emitter 30E can be directed to reflect or pass through tissue. Light detected by optical detector 30D can be suitably processed to generate selected data in accordance with various examples of the present subject matter.

System 600 can be configured for wearing on a body. In this example, system 600 is powered by a portable power supply, such as a battery. System 600 can be affixed to a body by a garment, a patch, or clamp device that remains in close proximity to the body for an extended duration.

Figure 7A:
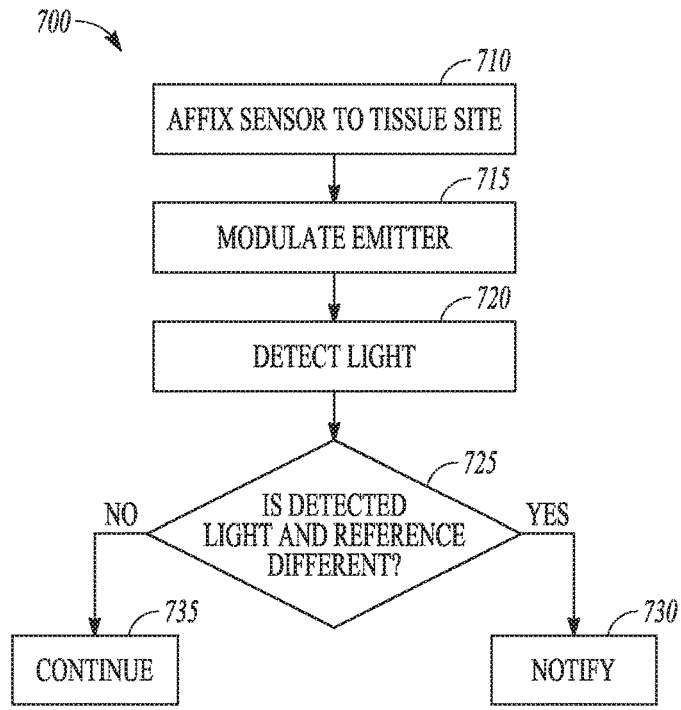
FIG. 7A includes a flow chart of a method, according to one example.

FIG. 7A includes a flow chart of method 700, according to one example. Method 700, at 710, includes affixing a sensor to a tissue site. The sensor can be affixed using an adhesive, a mechanical coupling, a garment, or other structure.

At 715, method 700 includes modulating an emitter, such as emitter 30E. Modulating the emitter includes driving the emitter to emit light at the tissue surface. In one example, processor 54 triggers modulation of emitter 30E.

At 720, method 700 includes detecting light using, for example, detector 30D. An electrical output signal from detector 30D can provide an indication of the light detected at a sense surface.

At 725, method 700 includes determining if the detected light differs from a reference. If the detected light and the reference differ, then, as shown at the 'yes' branch, method 700 proceeds to notify at 730. If the detected light and the reference do not differ, then, as shown at the 'no' branch, method 700 continues at 735. In one example, the detected light can include an external light signal unrelated to the modulated light from an emitter such as emitter 30E. The external light signal can correspond to an ambient light signal. The reference by which the detected light is compared can be a stored signal or represented by stored data. The reference can be stored in a memory. In one example, the reference includes previous data from the detector (such as detector 30D). The comparison at 725 can include comparing an AC absorption or a DC absorption and can be filtered to signal an interrupt on detection of a significant excursion or a significant change. Notification, at 730, can include storing data, such as a marker, in a local memory. In one example, notification, at 730, can include near instantaneous notification to a user by way of a tactile, visible, or audible alert. In one example, notification can include wirelessly transmitting a notification signal to a remote monitor. Continuing, at 735, can include returning to 715 in which the emitter is modulated or can include returning to 720 in which the light is detected.

In one example, method 700 entails processing the electrical output signal to generate a measure of a physiological parameter. In addition, processor 54 can execute analysis of the measured physiological parameter and, as a result of the analysis, provide a notification signal to the local device or to a remote device. For example, processor 54 can be configured to execute method 700 and determine if the sensor has been moved or placed on a different subject.

Figure 7B:
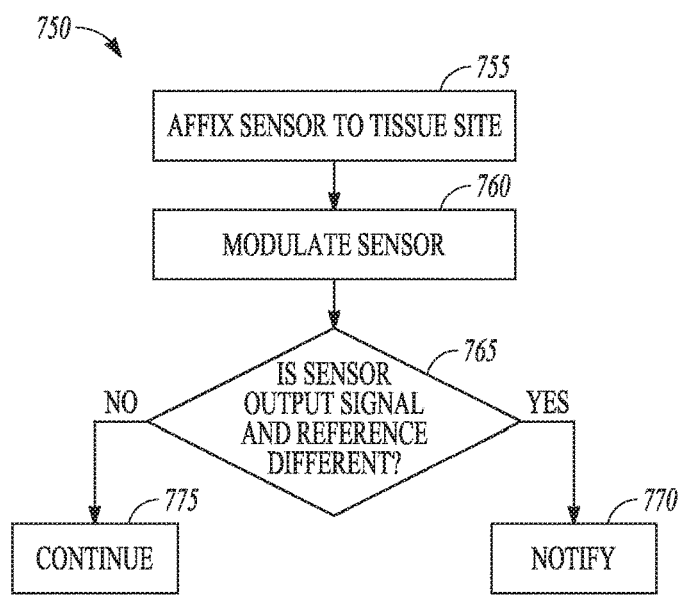
FIG. 7B includes a flow chart of a method, according to one example.

FIG. 7B includes a flow chart of method 750, according to one example. Method 750, at 755, includes affixing a sensor to a tissue site. The sensor can be affixed using an adhesive, a mechanical coupling, a garment, or other structure.

At 760, method 750 includes monitoring the sensor. In one example, monitoring entails processing the electrical output signal from a detector to generate a measure of a physiological parameter. Monitoring can also include processing the physiological parameter to discern occurrence of specified data.

At 765, method 750 includes determining if the sensor output signal differs from a reference. The sensor output signal and the reference both correlate with a detected light or both can correlate with the physiological parameter. As noted elsewhere, the reference can include stored data or can include previously detected data.

If a difference is detected, as shown at the 'yes' branch, then method 750 includes notification at 770. Notification can include alerting a user, storing data in a local memory, or transmitting a wireless notification signal to a remote device. If no difference is detected, as shown at the 'no' branch, then method 750 includes continuing at 775, which, according to one example, includes resuming processing at 760 monitoring sensor.

Notifying at 770 can include analysis of the physiological parameter and can include providing a notification signal to the local device or to a remote device.

In one example, the processor is configured to compare an output or physiological signal occurring at a time prior to detection of an interruption with a corresponding output or physiological signal occurring at a time following detection of an interruption. Such a comparison can determine if the sensor has been repositioned to a different site on a user or if the sensor has been repositioned from a first user to a second user.

An example of the present subject matter can provide a measure of oxygenation. In the context of home sleep studies, an example of the present subject matter can provide a measure that correlates with chain of custody considerations.

One example includes a patch-based, body-worn $SpO_2$ analysis device. For example, the device can be affixed to a patient while at a caregiver's facility. The device can be configured to detect adherence to the patient at periodic intervals. The frequency of these intervals can be tailored to ensure that the device cannot be removed and fitted to a different subject. In one example, the interval is approximately five seconds or less. The interval can be selected to achieve a battery longevity objective.

Processor 54 can be configured to implement a variety of algorithms to monitor and detect tampering or substitution. For example, an emitter, such as emitter 30D, can be pulsed at a periodic rate to establish a baseline absorption level for the user. The pulse can be configured for low power consumption. Processor 54 can be configured to monitor for an excursion in the absorption relative to the baseline absorption level. According to one example, an excursion in excess of an order of magnitude in the received photodiode current can be construed as indicative of a removed sensor event.

In one example, the system can be configured to pulse at least one emitter and monitor for a difference in the DC absorption ratios or in the AC absorption ratios.

In one example, the system can be configured to sample ambient light presented to the photodiode and monitor for an excursion. Other monitoring algorithms may be used in conjunction with this example in order to guard against defeat by removing the sensor in a dark room.

In one example, one or more emitters can be pulsed and processor 54 can be configured to monitor for the absence of a pulsatile signal.

In one example, a temperature sensor or a pressure sensor is coupled to processor 54. Temperature information or pressure information can be monitored for an excursion, and notification provided on detection.

Other sensors can also be used with various examples of the present subject matter. For example, a capacitance sensor or an inductance sensor can be monitored for an excursion.

In one example a bandage, wrap, or belt is provided with a tamper detector. The tamper detector provides an indication when the bandage, wrap, or belt is disturbed. Processor 54 can be configured to provide notification on detection of tampering. An example of a tamper detector can include a conductive material that breaks or disconnects an electrical circuit when removed.

In one example, a mechanical switch is held in a fixed position until the system is removed. Detection includes a change in state of the mechanical switch. Processor 54 can be configured to provide notification on detection of a change in state of the switch. In one example, electrically conductive pads (electrodes) are provided and an electrical impedance or electrical resistance through the user's tissue can be monitored. The sensor can provide an output corresponding to electrical impedance or resistance.

Various Notes & Examples

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A tamper resistant physiological sensor device comprising:
   a housing having a body contact surface configured for affixation to a tissue site of a body;
   an emitter coupled to the housing and having an emission surface and having an electrical terminal, the emission surface configured to emit light proximate the body contact surface in response to a signal applied to the electrical terminal;
   a detector coupled to the housing, the detector having a sense surface and an output terminal, the detector configured to provide an output signal on the output terminal in response to light detected at the sense surface, wherein the emission surface and the sense surface are in the same plane; and
   a processor coupled to the electrical terminal and coupled to the output terminal, the processor configured to implement an algorithm to monitor the output signal for an interruption between the body contact surface and the body and configured to generate an interrupt signal corresponding to the monitoring.

2. The device of claim 1 wherein the algorithm is configured to periodically determine absorption.

3. The device of claim 1 wherein the algorithm is configured to determine absorption and wherein the interrupt signal is generated in response to detecting an excursion from a baseline absorption.

4. The device of claim 1 wherein the algorithm is configured to determine a DC absorption ratio for the tissue site and wherein the interrupt signal is generated in response to detecting an excursion from a baseline absorption ratio.

5. The device of claim 1 wherein the algorithm is configured to determine an AC absorption ratio for the tissue site and wherein the interrupt signal is generated in response to detecting an excursion from a baseline absorption ratio.

6. The device of claim 1 wherein the algorithm is configured to detect light uncorrelated with light emitted from the emitter.

7. The device of claim 1 wherein the algorithm is configured to emit light from the emitter and wherein the interrupt signal is generated in response to absence of a pulsatile signal at the output terminal.

8. The device of claim 1 wherein a temperature sensor is coupled to the processor.

9. The device of claim 1 wherein a pressure sensor is coupled to the processor.

10. The device of claim 1 wherein a capacitance-based sensor is coupled to the processor.

11. The device of claim 1 wherein an impedance sensor is coupled to the processor.

12. The device of claim 1 wherein a resistance sensor is coupled to the processor.

13. The device of claim 1 wherein a conductivity sensor is coupled to the processor.

* * * * *